US012359554B2

(12) United States Patent
Alerigi et al.

(10) Patent No.: US 12,359,554 B2
(45) Date of Patent: Jul. 15, 2025

(54) REAL-TIME MULTIMODAL RADIOMETRY FOR SUBSURFACE CHARACTERIZATION DURING HIGH-POWER LASER OPERATIONS

(71) Applicant: Saudi Arabian Oil Company, Dhahran (SA)

(72) Inventors: Damian Pablo San Roman Alerigi, Al-Khobar (SA); Weichang Li, Katy, TX (US); Sameeh Issa Batarseh, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 647 days.

(21) Appl. No.: 17/201,618

(22) Filed: Mar. 15, 2021

(65) Prior Publication Data

US 2022/0290553 A1 Sep. 15, 2022

(51) Int. Cl.
*G01N 33/24* (2006.01)
*E21B 47/002* (2012.01)
(Continued)

(52) U.S. Cl.
CPC .......... *E21B 47/0025* (2020.05); *E21B 49/00* (2013.01); *G01N 21/47* (2013.01);
(Continued)

(58) Field of Classification Search
CPC .. E21B 47/0025; E21B 47/26; E21B 2200/22; E21B 49/00; G01N 33/24; G01N 2021/4709; G01N 2021/4792; G01N 21/47
See application file for complete search history.

(56) References Cited

U.S. PATENT DOCUMENTS 6,597,446 B2 7/2003 Klooster et al.
7,719,676 B2 5/2010 DiFoggio
(Continued)

OTHER PUBLICATIONS

San-Roman-Alerigi, Damian, Batatseh, Sameeh, Li, Weichang, and Haitham Othman. "Machine Learning and the Analysis of High-Power Electromagnetic Interaction with Subsurface Matter." Paper presented at the SPE Middle East Oil and Gas Show and Conference, Manama, Bahrain, Mar. 2019. (Year: 2019).*

(Continued)

*Primary Examiner* — Tarifur R Chowdhury
*Assistant Examiner* — Kemaya Nguyen
(74) *Attorney, Agent, or Firm* — Fish & Richardson P.C.

(57) ABSTRACT

Some implementations of the present disclosure provide a method that includes: irradiating a target surface with a process beam during a drilling process; in response to irradiating with the process beam, receiving a signal beam that contains light scattered from the target surface as well as light radiating from the target surface; splitting the signal beam into a first portion on a polarization arm and a second portion on a non-polarization arm; performing, on the polarization arm, a first plurality of polarization-dependent intensity and spectrum measurements of the first portion; performing, on the non-polarization arm, a second plurality of intensity and spectrum measurements of the second portion; and based on applying one or more machine learning techniques to at least portions of (i) the first plurality of polarization-dependent intensity and spectrum measurements, and (ii) the second plurality of intensity and spectrum measurements, determining a classification of the target surface.

20 Claims, 11 Drawing Sheets

(51) Int. Cl.
*E21B 49/00* (2006.01)
*G01N 21/47* (2006.01)

(52) U.S. Cl.
CPC ..... *G01N 33/24* (2013.01); *G01N 2021/4709* (2013.01); *G01N 2021/4792* (2013.01)

(56) References Cited

U.S. PATENT DOCUMENTS

| | | | |
|---|---|---|---|
| 8,826,973 | B2 | 9/2014 | Moxley et al. |
| 10,012,758 | B2 | 7/2018 | Speck et al. |
| 11,240,015 | B2* | 2/2022 | Cruz ........................ H04L 9/083 |
| 2003/0168257 | A1* | 9/2003 | Aldred ...................... E21B 44/00 175/24 |
| 2006/0012785 | A1 | 1/2006 | Funk et al. |
| 2008/0111064 | A1 | 5/2008 | Andrews et al. |
| 2010/0044103 | A1 | 2/2010 | Moxley et al. |
| 2013/0063569 | A1* | 3/2013 | Sato ...................... H04N 13/218 348/46 |
| 2013/0237797 | A1* | 9/2013 | Muller .................... G01N 21/49 600/407 |
| 2014/0240951 | A1 | 8/2014 | Brady et al. |
| 2015/0253192 | A1* | 9/2015 | Sano ..................... G02B 5/3083 356/364 |
| 2016/0115778 | A1* | 4/2016 | van Oort ................ G06N 20/00 175/27 |
| 2016/0258741 | A1* | 9/2016 | Perkins ................. G01N 21/211 |
| 2018/0156600 | A1 | 6/2018 | Cable et al. |
| 2020/0134773 | A1 | 4/2020 | Pinter et al. |
| 2020/0319108 | A1 | 10/2020 | Butte et al. |
| 2021/0132356 | A1* | 5/2021 | Gaiduk .............. G02B 27/1066 |
| 2022/0187493 | A1* | 6/2022 | Smith .................... G01V 1/284 |

OTHER PUBLICATIONS

Antony et al., "Photonics and fracture toughness of heterogeneous composite materials," 2017, Scientific Reports, 7:4539, 8 pages.
Batarseh et al., "Downhole high-power laser tools development and evolutions," presented at the Abu Dhabi International Petroleum & Exhibition Conference, Abu Dhabi, United Arab Emirates, Nov. 12-15, 2018, 15 pages.
Batarseh et al., "High power laser application in openhole multiple fracturing with an overview of laser research; Past, present and future," presented at the SPE Saudi Arabia Section Technical Symposium and Exhibition, Khobar, Saudi Arabia, Apr. 8-11, 2012, Society of Petroleum Engineers, 10 pages.
Batarseh et al., "LaserGun: The Next Perforation Technology," presented at the SPE Middle East Oil & Gas Show and Conference, Manama, Bahrain, Mar. 18-21, 2019, 15 pages.
Batarseh et al., "Microwave With Assisted Ceramic Materials to Maximize Heat Penetration and Improve Recovery Efficiency of Heavy Oil Reservoirs," presented at the SPE Middle East Oil & Gas Show and Conference, Kingdom of Bahrain, Mar. 6-9, 2017, 24 pages.
Batarseh et al., "Well Perforation Using High-Power Lasers," presented at the SPE Annual Technical Conference and Exhibition, Denver, Colorado, Oct. 5-8, 2003, 10 pages.
Boinott et al., "High resolution geomechanical profiling in heterogeneous source rock from the Vaca Muerta Formation, Neuquén Basin, Argentina," presented at the 52nd US Rock Mechanics/ Geomechanics Symposium, Seattle, Washington, USA, American Rock Mechanics Association, Jun. 17-20, 2018, 8 pages.
Frank, "Discriminating between coherent and incoherent might with metasurfaces," Jul. 2018, 11 pages.
Graves et al., "StarWars Laser Technology for Gas Drilling and Completions in the 21st Century," presented at the SPE Annual Technical Conference and Exhibition, Houston, Texas, Oct. 3-6, 1999, 10 pages.
Graves et al., "Temperatures Induced by High Power Lasers: Effects on Reservoir Rock Strength and Mechanical Properties," presented at the SPE/ISRM Rock Mechanics Conference, Irvine, Texas, Oct. 20-23, 2002, 7 pages.
Guo et al., "Convolutional Neural Networks for Steady Flow Approximation," presented at the 22nd ACM SIGKDD International Conference on Knowledge Discovery and Data Mining— KDD, San Francisco, California, Aug. 13-17, 2016, 10 pages.
Mutyala et al., "Microwave applications to oil sands and petroleum: A review," Fuel Process Technol, 2010, 91:127-135.
Nourbakhsh et al., "Embedded sensors and feedback loops for iterative improvement in design synthesis for additive manufacturing," presented at the ASME 2016 International Design Engineering Technical Conference and Information in Engineering Conference, Charlotte, NC, 9 pages.
Principles of Optics: Electromagnetic Theory of Propagation, Interference and Diffraction of Light, Born et al., 6th ed. Pergamon Press, 808 pages.
Salehi et al., "Laser drilling—drilling with the power of light," Gas Technology Institute Report, 2000-2007 period report, Chicago, IL, 318 pages.
San-Roman-Alergi et al., "Machine learning and the analysis of high-power electromagnetic interaction with subsurface matter," presented at the SPE Middle East Oil and Gas Show and Conference, Manama, Bahrain, Mar. 18-21, 2019, 11 pages.
San-Roman-Alerigi et al., "Geomechanical and thermal dynamics of distributed and far-field dielectric heating of rocks assisted by nano-enablers—A numerical exploration," presented at the SPE Abu Dhabi International Petroleum Exhibition and Conference, Abu Dhabi, UAE, Nov. 13-16, 2017, 21 pages.
San-Roman-Alerigi et al., "Numerical Modeling of Thermal and Mechanical Effects in Laser-Rock Interaction—An Overview," presented at the 50th U.S. Rock Mechanics/Geomechanics Symposium, Houston, TX, Jun. 26-29, 2016; American Rock Mechanics Association, 2016, 11 pages.
towarddatascience.com [online], "Support vector machine— introduction to machine learning algorithms," Ghandi, Jul. 7, 2018, retrieved May 19, 2021, retrieved from URL <https://towardsdatascience. com/support-vector-machine-introduction-to-machine-learning-algorithms-934a444fca47>, 12 pages.
towardsdatascience.com [online], "K-Means Clustering— Explained," Yildrim, Mar. 2020, retrieved on May 19, 2021, retrieved from URL <https://towardsdatascience.com/k-means-clustering-explained-4528df86a120#:~:text=K%2Dmeans%20clustering% 20aims%20to,methods%20to%20measure%20the%20distance>, 12 pages.
Vaferi et al., "Modeling and analysis of effective thermal conductivity of sandstone at high pressure and temperature using optimal artificial neural networks," Journal of Petroleum Science and Engineering, 2014, 119, 10 pages.
Zinati, "Using Distributed Fiber-Optic Sensing Systems to Estimate Inflow and Reservoir Properties," Technische Universiteit Delft, 2014, 135 pages.

* cited by examiner

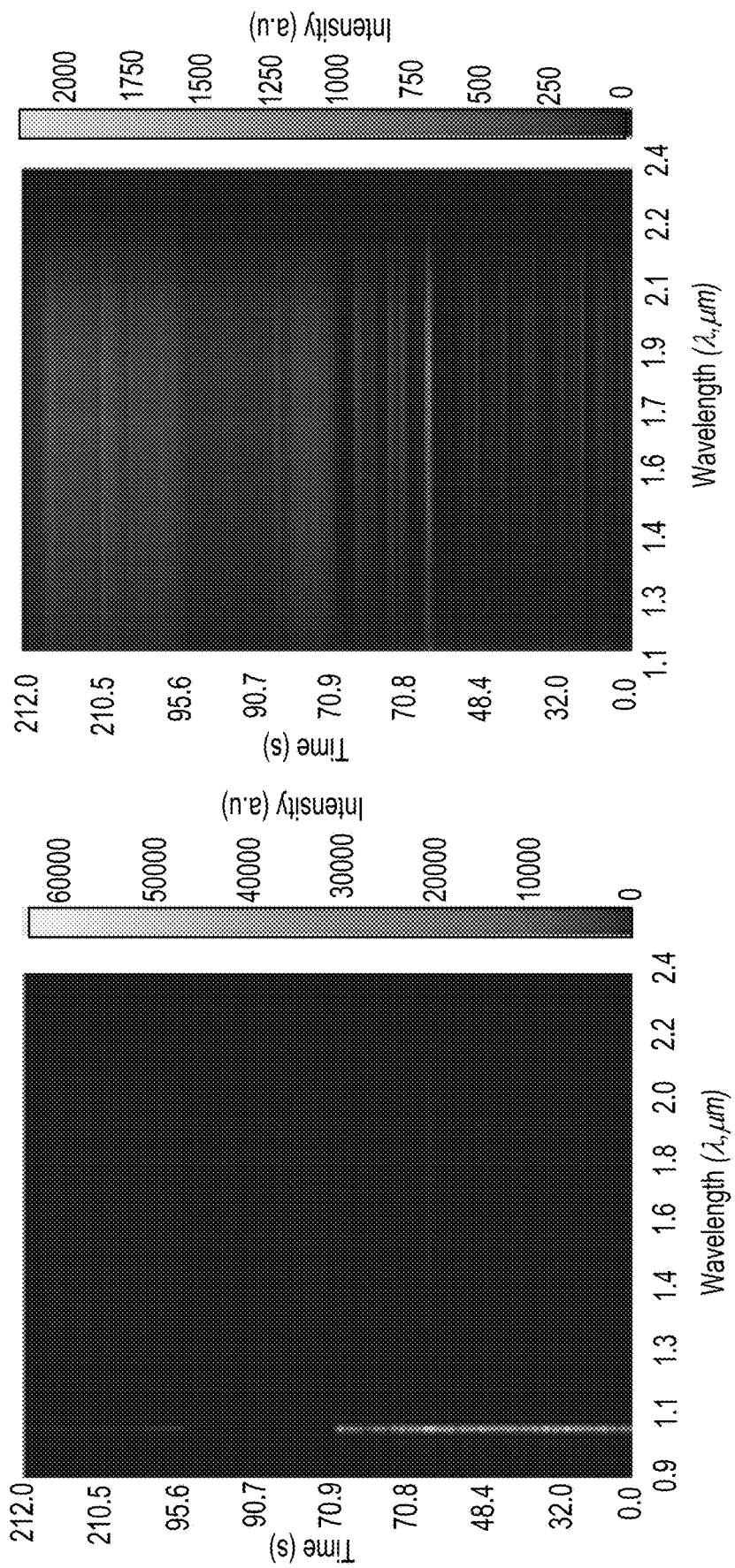

REAL-TIME MULTIMODAL RADIOMETRY FOR SUBSURFACE CHARACTERIZATION DURING HIGH-POWER LASER OPERATIONS

TECHNICAL FIELD

This disclosure generally relates to rock characterization and classification during a drilling process.

BACKGROUND

Rock, in geology, refers to naturally occurring and coherent aggregate of one or more minerals. Such aggregates constitute the basic unit of which the solid Earth is composed. The aggregates typically form recognizable and mappable volumes. Characterization and classification of rocks can reveal insights about the layered formation, including fluid saturation, of the solid Earth during a drilling operation in the context of gas and oil exploration.

SUMMARY

In one aspect, some implementations provide a method that includes: irradiating a target surface with a process beam during a drilling process; in response to irradiating with the process beam, receiving a signal beam that contains light scattered from the target surface as well as light radiating from the target surface; splitting the signal beam into a first portion on a polarization arm and a second portion on a non-polarization arm; performing, on the polarization arm, a first plurality of polarization-dependent intensity and spectrum measurements of the first portion; performing, on the non-polarization arm, a second plurality of intensity and spectrum measurements of the second portion; and based on applying one or more machine learning techniques to at least portions of (i) the first plurality of polarization-dependent intensity and spectrum measurements, and (ii) the second plurality of intensity and spectrum measurements, determining a classification of the target surface.

Implementations may include one or more of the following features.

The implementation may further include: determining a status of the drilling process; and predicting at least one of: a type of an incoming rock, an outcome of the drilling process, a parameter for performing the first plurality of polarization-dependent intensity and spectrum measurements, or a parameter for performing the second plurality of intensity and spectrum measurements.

The one or more machine learning techniques may include: identifying a first set of features from the first plurality of polarization-dependent intensity and spectrum measurements and a second set of features from the second plurality of intensity and spectrum measurements; and combining the first set of features and the second set of features in determining the classification of the target surface. The method may further include: establishing a database of the first set of features and the second set of features, wherein the first set of features and the second set of features in combination differentiate two or more types of the target surface. The method may further include: applying the database while applying the one or more machine learning techniques to the at least portions of (i) the first plurality of polarization-dependent intensity and spectrum measurements, and (ii) the second plurality of intensity and spectrum measurements.

The one or more machine learning techniques may include: a boosting technique, a K-means clustering technique, and a Support Vector Machine (SVM) technique. The method may further include: visualizing the classification of the target surface using a t-distribution stochastic neighbor embedding (tSNE) technique. The first plurality of polarization-dependent intensity and spectrum measurements may include a first intensity measurements on a first branch and a second intensity measurements on a second branch. The first and second intensity measurements may be cross-polarized. The first and second branches may originate from a polarization beam splitter on the polarization arm. The method may further include: capturing, on the non-polarization arm, a plurality of images based on the second portion of the signal beam; and determining a luminosity based on a histogram of the plurality of images. The method may further include: applying the one or more machine learning techniques to the luminosity in addition to the at least portions of (i) the first plurality of polarization-dependent intensity and spectrum measurements, and (ii) the second plurality of intensity and spectrum measurements; and based on results from the one or more machine learning techniques, determining at least one of: a classification of the target surface and a status of the drilling process.

In another aspect, some implementations provide a system that includes: an optical system that includes: a laser source; a polarization arm; and a non-polarization arm; and an analyzer in communication with optical system, wherein the system is configured to perform operations of: irradiating a target surface with a process beam from the laser source during a drilling process; in response to irradiating with the process beam, receiving a signal beam that contains light scattered from the target surface as well as light radiating from the target surface; splitting the signal beam into a first portion on the polarization arm and a second portion on the non-polarization arm; performing, on the polarization arm, a first plurality of polarization-dependent intensity and spectrum measurements of the first portion; performing, on the non-polarization arm, a second plurality of intensity and spectrum measurements of the second portion; and based on applying one or more machine learning techniques on the analyzer to at least portions of (i) the first plurality of polarization-dependent intensity and spectrum measurements, and (ii) the second plurality of intensity and spectrum measurements, determining a classification of the target surface.

Implementations may include one or more of the following features.

The operations may further include: determining a status of the drilling process; and predicting at least one of: a type of an incoming rock, an outcome of the drilling process, a parameter for performing the first plurality of polarization-dependent intensity and spectrum measurements, or a parameter for performing the second plurality of intensity and spectrum measurements.

The one or more machine learning techniques may include: identifying a first set of features from the first plurality of polarization-dependent intensity and spectrum measurements and a second set of features from the second plurality of intensity and spectrum measurements; and combining the first set of features and the second set of features in determining the classification of the target surface. The operations may further include: establishing a database of the first set of features and the second set of features, wherein the first set of features and the second set of features in combination differentiate two or more types of the target surface. The operations may further include: applying the database while applying the one or more machine learning techniques to the at least portions of (i) the first plurality of polarization-dependent intensity and spectrum measurements, and (ii) the second plurality of intensity and spectrum measurements.

The one or more machine learning techniques may include: a boosting technique, a K-means clustering technique, and a Support Vector Machine (SVM) technique. The operations may further include: visualizing the classification of the target surface using a t-distribution stochastic neighbor embedding (tSNE) technique. The first plurality of polarization-dependent intensity and spectrum measurements may include first intensity measurements on a first branch and second intensity measurements on a second branch, wherein the first and second intensity measurements are cross-polarized, and wherein the first and second branches originate from a polarization beam splitter on the polarization arm. The operations may further include: capturing, on the non-polarization arm, a plurality of images based on the second portion of the signal beam; and determining a luminosity based on a histogram of the plurality of images. The operations may further include: applying the one or more machine learning techniques to the luminosity in addition to the at least portions of (i) the first plurality of polarization-dependent intensity and spectrum measurements, and (ii) the second plurality of intensity and spectrum measurements; and based on results from the one or more machine learning techniques, determining at least one of: a classification of the target surface and a status of the drilling process.

Implementations according to the present disclosure may be realized in computer implemented methods, hardware computing systems, and tangible computer readable media. For example, a system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The details of one or more implementations of the subject matter of this specification are set forth in the description, the claims, and the accompanying drawings. Other features, aspects, and advantages of the subject matter will become apparent from the description, the claims, and the accompanying drawings.

DESCRIPTION OF DRAWINGS

FIGS. 3A-3B illustrate examples of the real-time and in-situ reflectance data as gathered by an in-line spectrometer according to an implementation of the present disclosure.

Like reference numbers and designations in the various drawings indicate like elements.

DETAILED DESCRIPTION

Figure 1:
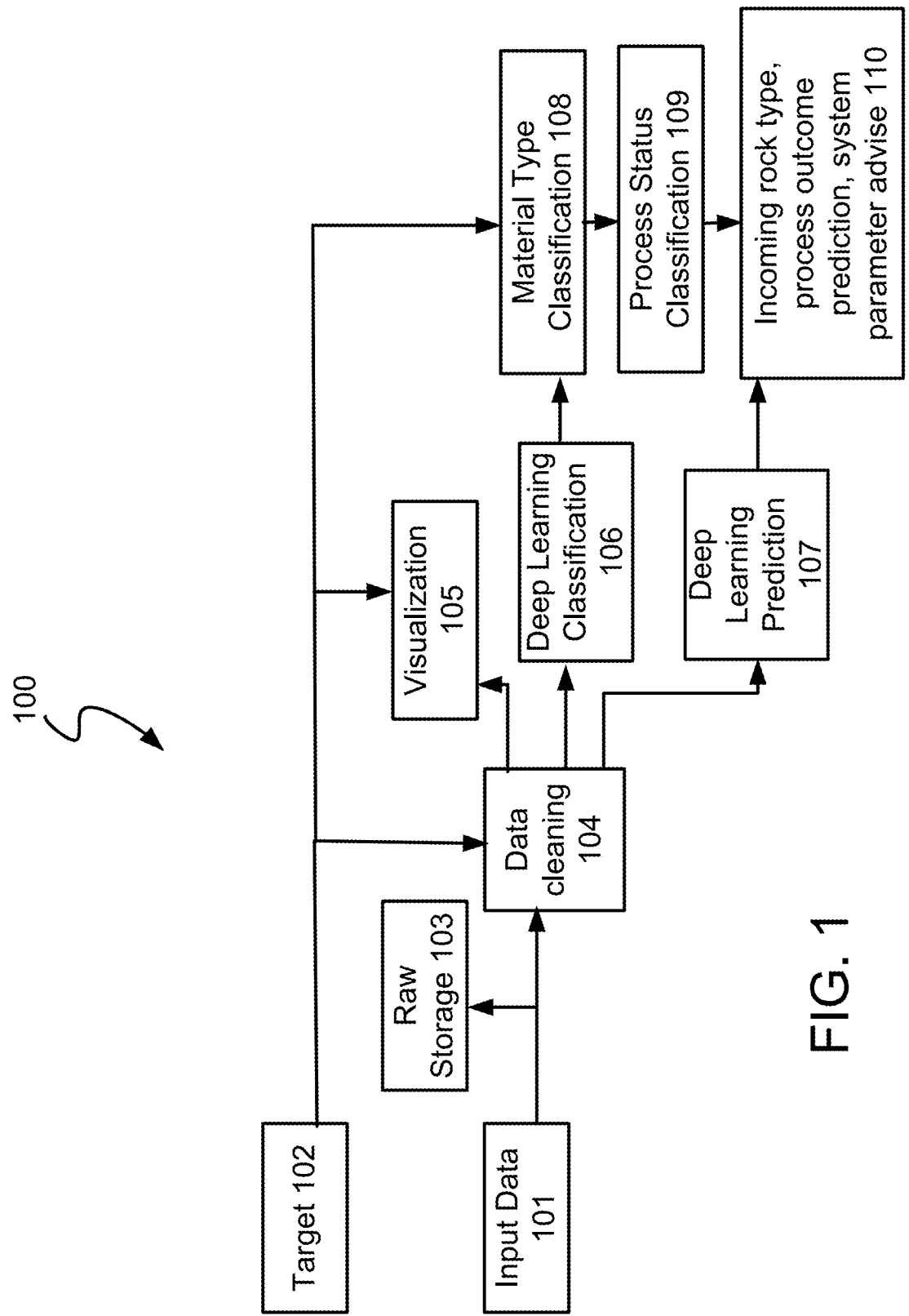
FIG. 1 shows an example of a work flow of leveraging high power laser for mineral type classification and process status classification according to an implementation of the present disclosure.

The disclosed technology is directed to a real-time and in-situ computerized method to classify rock type and characterize the interaction of high power lasers with subsurface matter during a drilling operation. Some implementations can include passive or active methods that are based on the luminosity and spectral analysis of reflected, scattered and black body radiation. In these implementations, the optical analysis can combine non-polarized and cross-polarized spectral information in a compact form. In addition, the implementations enable the characterization of images taken from a charge-coupled device (CCD) or a complementary metal-oxide-semiconductor (CMOS) on one arm of the optical system. For example, cross-polarized luminosity can provide an estimation of the process and coupling between the laser and the substrate. In these implementations, the cross-polarization can characterize the performance of the drilling process. The cross-polarized spectral information carries information about the rock composition, fluids, and some mechanical properties. Some implementations incorporate real-time multimodal methods to characterize rock type and interaction with subsurface materials. Some implementations may incorporate machine learning techniques including, e.g., boosting, k-means clustering, Support Vector Machine (SVM), t-distribution Stochastic Neighbor Embedding (tSNE), to support realtime characterization. The implementations may incorporate additional machine learning routines to mine and understand the data using an artificial recurrent neural network, e.g., gated recurrent units (GRU) or long short-term memory (LSTM). Some implementations may additionally incorporate a feedback loop to calibrate and fine-tune the machine learning techniques.

The terminology used in the present disclosure includes the following terms.

The term "HPL" refers to high power laser. HPL can include pulsed or continuous wave (CW) laser or a plurality of lases with high energy. The term high power refers to lasers with peak power at or above 100 Watts. Typical HPLs for subsurface operations have peak power at or above 10 kW. HPL can be in the visible and infrared range with a wavelength, for example, from 600 nm to 10000 nm.

The term "process status" refers to a status of a process. Examples can include glass forming, process failure/success/completion, etc.

The term "Spallation" refers to a process in which fragments of material (i.e., spall) are ejected from a body due to impact or stress. In geology, the term refers to the separation of fragments from the surface of a rock, especially by interaction with a compression wave.

The term "machine learning analytics" refers to the use of machine learning and applied statistics to predict unknown conditions based on the available data. Two general areas that fall under machine learning analytics are classification and regression. While classification refers to the prediction of categorical values, regression connotes the prediction of continuous numerical values. One machine learning implementation is also known as "supervised learning" where the "correct" target or y values are available. For illustration, the goal of some implementations is to learn from the available data to predict the unknown values with some defined error metrics. In supervised learning, for example, there are a set of known predictors (features) $x_1, x_2, \ldots, x_m$ which are known to the system as well as the target values $y_1, y_2, \ldots, y_n$, which are to be inferred. The system's objective is to train a machine learning model to predict new target values $y_1, y_2, \ldots, y_n$ by observing new features.

The implementations can employ a variety of machine learning algorithms. For classification, examples of prediction algorithms can include, logistic regression, decision trees, nearest neighbor, support vector machines, K-means clustering, boosting, and neural networks. For regression, examples of predication algorithms can include least squares regression, Lasso, and others. The performance of an algorithm can depend on a number factors, such as the selected set of features, training/validation method and hyper-parameters tuning. As such, machine learning analytics can manifest as an iterative approach of knowledge finding that includes trial and error. An iterative approach can iteratively modify data preprocessing and model parameters until the result achieves the desired properties.

Referring to FIG. 1, an example of a workflow diagram 100 is shown for realtime mineral type classification and process status classification using high power laser (HPL). An HPL laser source may have its power and spectral signature. As illustrated, input data 101 may include luminosity data and spectrometry data. Input data 101 may additionally include data from other sensors, such as environmental sensors and purging sensors. Environmental sensors may include temperature sensors and pressure sensors. Purging sensors may include flow speed and pressure sensors, and fluid type sensors.

Input data 101 may feed raw storage 103 and data cleaning module 104. Raw storage 102 can encompass any type of data storage device configured to store record input data during a drilling process. In some cases, raw storage 102 can record input data in a variety of formats. Raw storage 102 can reach Terabyte or more. The recorded data can be retrieved for off-line analysis to fine tune a realtime data analysis engine based on machine learning.

Figure 2A:
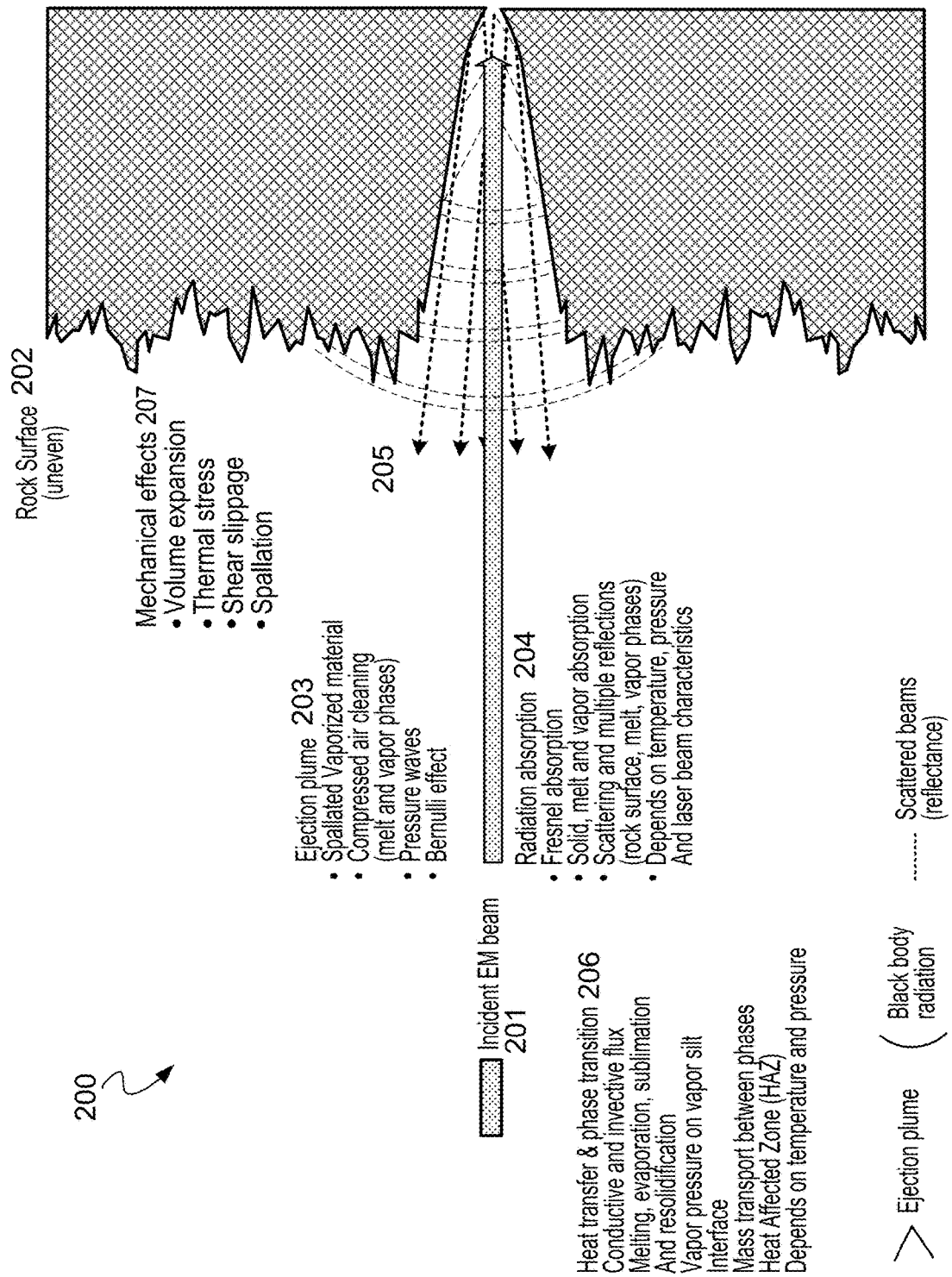
FIG. 2A is a diagram illustrating physical dynamics when an electromagnetic (EM) beam is incident on rock surface according to an implementation of the present disclosure.

Further referring to FIG. 2A, diagram 200 summarizes physical dynamics when an electromagnetic (EM) beam 201 is incident on rock surface 202. The interaction between the electromagnetic (EM) field and the material results in the absorption, transmission, reflection, and scattering of the incoming beam 201. All of these effects take place concurrently and in different proportions. The processes can depend on the physical properties of the material, the environment, and the EM field. Rocks are made of mineral materials which are polycrystalline and morphologically amorphous; thus, the beam propagates through a volume made of multiple interfaces produced by these inhomogeneities or imperfections. As the incident beam 201 makes impact with the rock surface 202, rock surface 202 may experience mechanical effects 207 including, for example, volumetric expansion, thermal stress, shear slippage, and spallation. As the incident beam 201 propagates through the material, ejection plume 203 may also be present, including, for example, spallated/vaporized material, compressed air cleaning (melt and vapor phases), pressure waves, and Bernoulli effect.

Additionally, the beam undergoes refraction (deviation from the direction of the incident beam), diffraction (spread out of the beam due to imperfections or voids), regular reflection (specular reflection), and scattering (e.g. diffuse reflection). The absorption, diffraction, and scattering processes occur within a volume of the material, rather than strictly at the surface. This is because as the light interacts with the material first, light will be partially reflected, absorbed, and scattered by the first particles at the surface (e.g., surface 202); the light scattered forward will interact with the particle beneath and undergo a similar process. This cascading process takes place within a few micrometers inside the material. The net result is an absorption volume and light scattered in multiple directions, even for a beam at normal incidence.

The scattered and reflected light carry information that can be analyzed to determine the properties of the material. Depending on the wavelength of the incident beam, the information may include surface topology, phase state, electromagnetic properties, and chemical composition. Meanwhile, the portion of the beam that is absorbed will typically transform into thermal energy (heat). Depending on the energy of the electromagnetic (EM) excitation, the heat might be enough to warm, melt, disassociate, spallate, evaporate, and even sublimate the material. Heat dissipation takes place through radiation (black body) and convection, with the former providing additional data about the material.

As illustrated, radiation absorption 204 can include Fresnel absorption, solid, melt, and vapor absorption, scattering and multiple reflections that depend on temperature, pressure, and laser beam characteristics. The scattered beams 205 can represent reflections of the incident beam 201. The incident beam 201 can additionally induce heat transfer and phase transition 206 including, among others, conductive and convective flux, melting, evaporation, sublimation and resolidification, vapor pressure on vapor/rock interface, mass transport between phases, heat affected zone (HAZ), each may depend on pressure and temperature.

These interlinked dynamics can be leveraged to provide insight into the material properties, the interaction, and the environment. The rate of electromagnetic absorption, reflection, scattering, and thermal transport depends on the thermal, electromagnetic, and mechanical properties of the material and its surroundings. Some implementations may identify the properties of the material, characterize the electromagnetic excitation mechanisms (electronic, atomic, and molecular), and measure the thermal transport processes (advection, conduction, convection, and radiation). In these implementations, subsurface photonic technologies can shed additional light on the underlying formation before, during, and after the process. Indeed, combined with machine learning and statistical analysis, some implementations can evaluate the process, characterize the formation (logging), and optimize HPL applications.

Figure 2B:
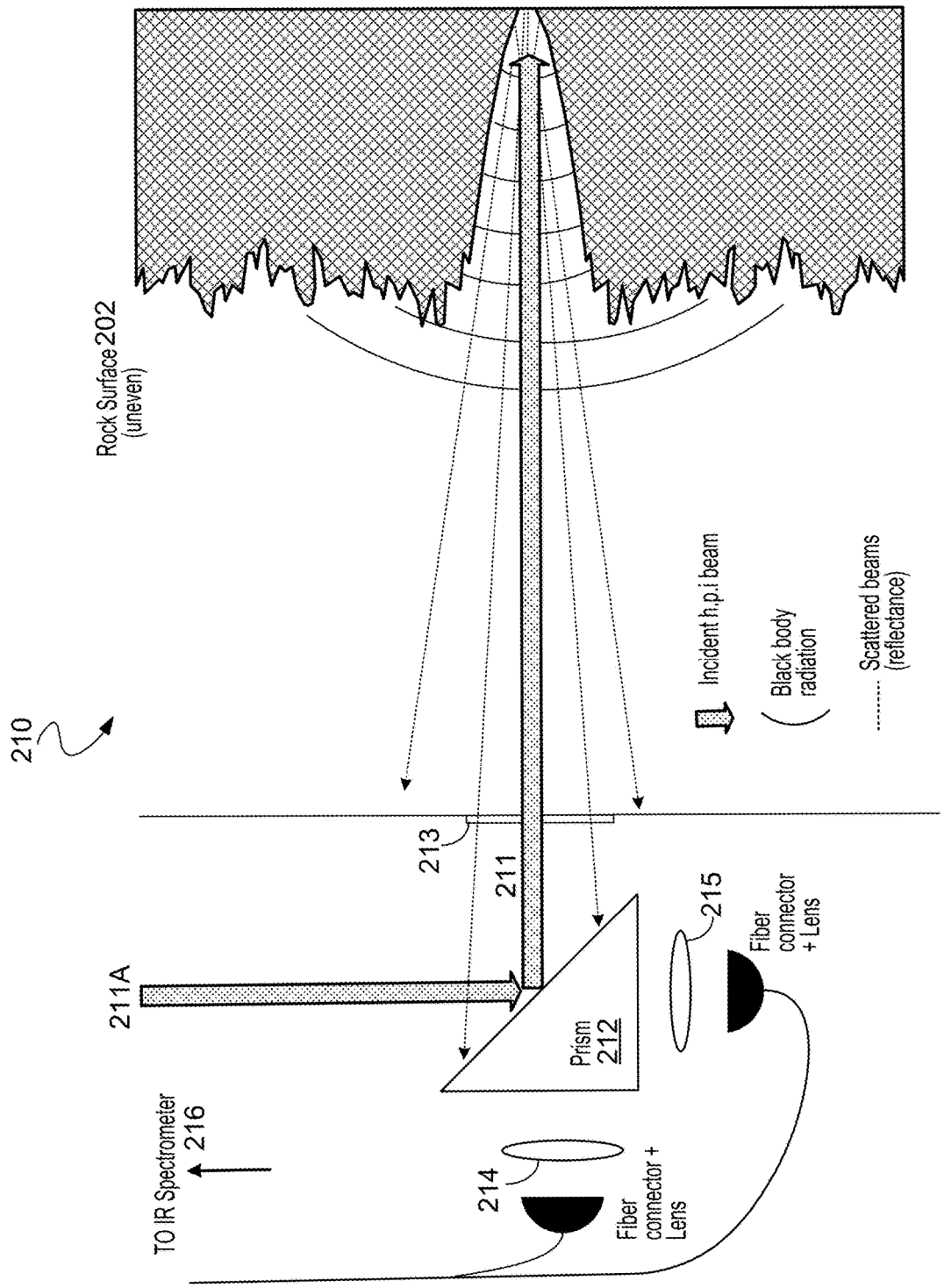
FIG. 2B is a diagram illustrating an example of a high power laser configuration and the physical dynamics for the high power laser incident on the rock surface according to an implementation of the present disclosure.
Figure 2C:
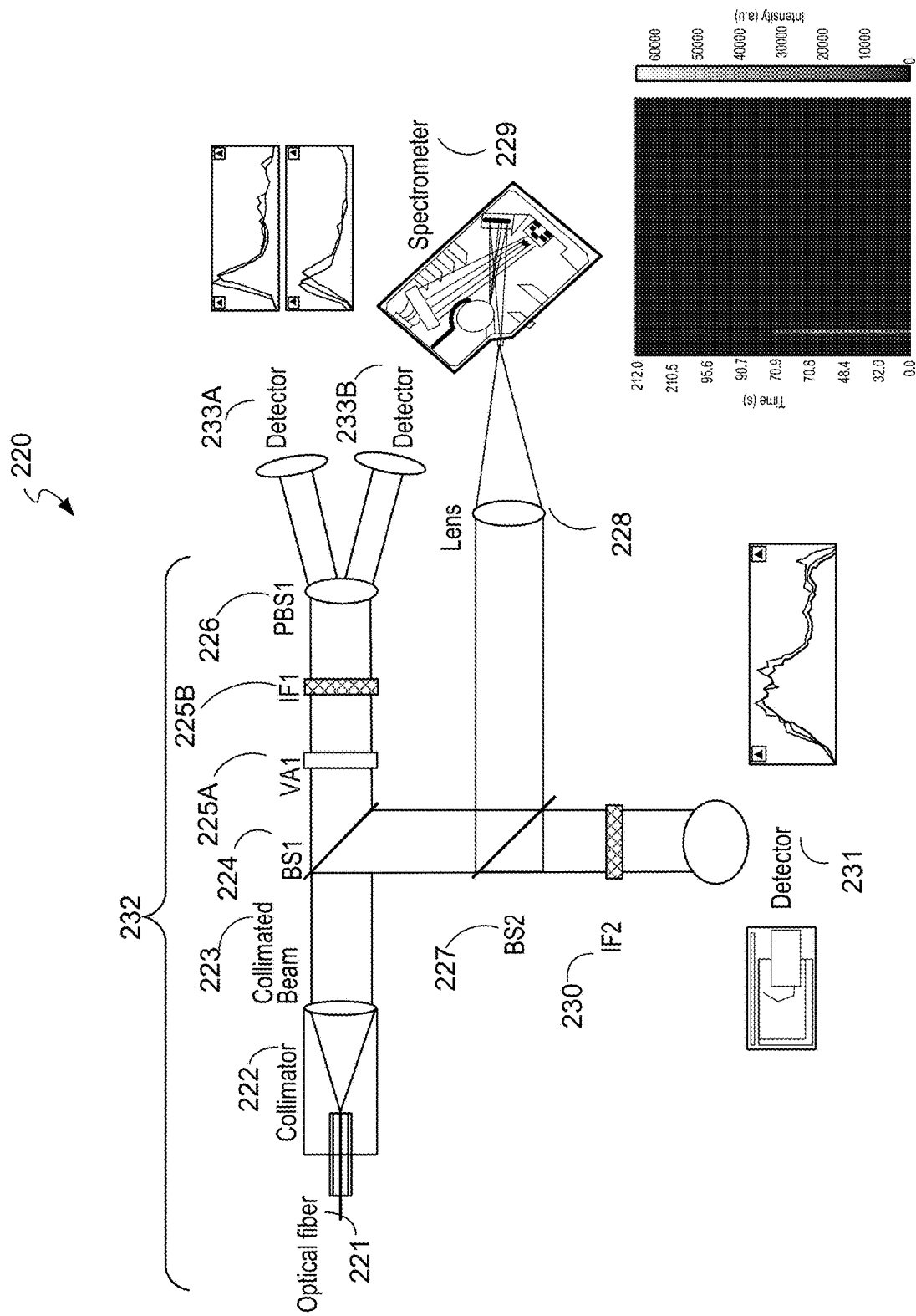
FIG. 2C is a diagram illustrating an example of a high power laser system for evaluation of overall luminosity that includes back-reflection and infrared blackbody radiation according to an implementation of the present disclosure.

Further referring to FIGS. 2B and 2C, diagram 210 and 220 each depict a configuration of a high power laser system. Diagram 210 shows that a laser beam 211A from a high power laser source reaches prism 212 and then deflects as beam 211 to illuminate the target (rock surface 202). Laser beam 211A may travel through window 213 before reaching the target. The exiting beam impinges on the rock and/or downhole media (target). The laser beam 211A may be a process beam (i.e. high power near-infrared laser). The laser beam 211A can also include several laser beams at different frequencies, which can be selected to excite different molecular bonds in target material. The laser beam 211A may be pulsed or continuous.

Non-coupled laser light is scattered diffusively from the target. A portion of this radiation is back-scattered through the optical path of incidence. This light enters the prism 212 and is diffracted in different directions. A portion of the light can be collected at the opposite end, for example, by lens-coupler assembly 215. A major portion of the high power laser beam can be reflected as beam 211 that impinges on the target surface 202. The irradiation can generate a plasma and warm up the rock, both effects can generate blackbody radiation. A portion of this radiation also propagates back to window 213, and transmits back to the prism 212. This light can also be collected at the opposite end, for example, by lens-coupler assembly 214. As such, during the drilling operation, a portion of the back-scattered laser light and black-body radiation can be collected in realtime. As illustrated, the coupler directs the radiation to a conveyance umbilical (optical fiber) that connects to analyzer 216, which can operate remotely. In some cases, the analyzer 216 is on the measurement site, in which case the coupler can transmit the collected light directly to analyzer 216. The process beam thus generates a signal beam, which be directly analyzed and its characteristics saved for computational correlation.

In FIG. 2C, diagram 220 additionally shows a sensing package that includes an optical package 232, radiometer sensors 233A and 233B, a spectrometer 229, a charge coupled device/complementary metal oxide semiconductor (CCD/CMOS) sensor 231. The optical package 232 can include optical fiber 221 that out-couples light from the conveyance umbilical. The out-coupled light is then collimated by collimator 222 to generate collimated beam 223. The out-coupled light is also known as the signal beam, which then enters the optical processing unit and goes through different stages in parallel.

Beam splitter 224 may split the signal beam. Portions of the signal beam may traverse variable attenuator 225A, interference filter 225B, and then enter polarization beam splitter 226. Variable attenuator 225A is configured to reduce the luminosity of the beam and reduce saturation of the downstream sensors. Interference filter 225B is an active component configured to provide a band-pass filter that allows a certain wavelength range within the beam to be transmitted. Polarizing beam splitter 226 can split the transmitted beam into, for example, circular left and right polarizations and then direct the circularly polarized beam respectively to radiometer sensors 233A and 233B for intensity measurement. Detectors 223A and 223B can also be replaced by spectrometers. In this last case, the system performs a cross-polarized spectral measurement. The total intensity can then be calculated from the sum of the integrals over the wavelengths measured by each spectrometer. The output of the polarized analysis can be plotted in a Poincare sphere to record polarization and intensity over time.

Other portions of the signal beam may be further split by beam splitter 227. One part of the beam may traverse lens 228 and then couple to spectrometer 229. In some cases, a scanning spectrometers, such as an Ocean Optics NIRQuest 2500 or Ocean Insight HR4Pro XR models can be used. In other cases the spectrometer 229 may be a Fourier-transform spectrometer, such as Agilent 4100 ExoScan FTIR. In other instances both spectrometers could be used in conjunction. In addition, in some implementation lens 228 may be exchanged for a polarized beam splitter, similar to 226, and the two polarized beams pass through to coupling lenses into two scanning or Fourier-transform spectrometers, one for each arm. The polarization characterization provides the distribution of intensity as a function of wavelength and can be stored as well as a function of time. FIGS. 3A and 3B show examples of spectral measurement taken as snapshots of a respective wavelength range (horizontal axis) at various time points (vertical axis). In these measurements, the time resolution may generally depend on the refresh-rate of the electronics and sensors in the spectrometer. In some cases, the time resolution can be on the order of 1 ms.

The other part of the beam, which is non-polarized, may traverse active interference filter 230 and then couple to a charge coupled device/complementary metal oxide semiconductor (CCD/CMOS) sensor 231. This sensor type can enable the capturing of images at the focal plane of a coupling lens. The luminosity content of the images can be calculated to generate histograms. The images can further be analyzed for pattern recognition and assessment/classification of objects. For example, sensor 231 can perform high-speed imaging of high power laser (HPL) processes (perforation, multi-string cuttings, de-scaling) and provide information to control the tool, evaluate the job, and support the development of next-gen automated HPL tools. Additionally or alternatively, a radiometer sensor can be used. Interference filter 230 is again an active component that provides a band-pass filter on the beam. This band-pass filter allows a certain wavelength range to pass into the next stage. Active interference filters can cycle over different wavelength ranges or be fully turned-off. Alternatively or additionally, the configuration can include a combination of a variable attenuator and/or filters (band-pass, short-pass, or long-pass) that allow the characterization of specific section of the image within a given wavelength/frequency range. The combined measurement data is stored (raw), processed, and analyzed (real time and al-posteriori).

Returning to FIG. 1, data cleaning module 104 can pre-process the raw data in raw storage 102 for subsequent processing. For example, data cleaning module 104 can remove spurious measurements from the raw data. Data module 104 may additionally perform normalization on the raw data. Data module 104 may further perform integration of data from different sensors. For example, data from various sensors can be synchronized, cross-correlated, and weighted.

Target 102 is a set of parameters encoding the objective of data analysis (including classification and prediction). The parameters can include rock/material type, for example, sandstone, limestone, shale, scale, etc. The parameters can include process status, for example, glass forming, and process failure/success/completion. Other parameters can also be included, for example, organic content type, fluid type, and tool status.

Based on the output from data cleaning module 104 and input from target 102, visualization 105 may present the measurement data. In various implementations, the data generated by the radiance detectors provide information about the intensity distribution of the back-scattered light. This data can be analyzed in real-time to identify change in substrate material (e.g. changing from rock to steel), identify formation of glass (e.g., a left-skewed distribution), poor coupling of laser beam (e.g., a left-skewed distribution on a polarization dependent chart), and assess the process' performance (e.g., performance becomes adequate when more than a threshold amount of light is absorbed and no glass forms, i.e. a right-skewed or centered luminosity distribution).

The data generated by the spectrometer 229 provides information of intensity as a function of wavelength, the examples of which can be found in FIGS. 3A and 3B. For example, FIG. 3A shows a spectrogram that displays the optical spectrum (horizontal axis in unit of μm) at various measurement times (vertical axis in unit of second). FIG. 3A includes the wavelength that corresponds to the operating wavelength of the laser source (i.e., $\lambda=1.064\pm0.01$ μm). FIG. 3B shows the filtered spectral data above the laser wavelength (i.e., $\lambda>1.1$ μm). Here, the spectral data can be readily analyzed to identify rock types and assess process performance, and predict geomechanical and/or geochemical properties of the probed rock samples.

Indeed, implementations may include analysis unit & neural engine that include a set of electronics configured compute and analyze the signal from radiometer and spectrometer. This unit may perform advanced analysis enabled by machine learning techniques (neural engine) and provide some feedback.

Based on the output from data cleaning module 104, deep learning classification 106 can perform material type classification 108 and process status classification 109, while deep learning prediction 107 can generate predictions 110 for incoming rock type, process outcome, and system parameter.

Figure 4A:
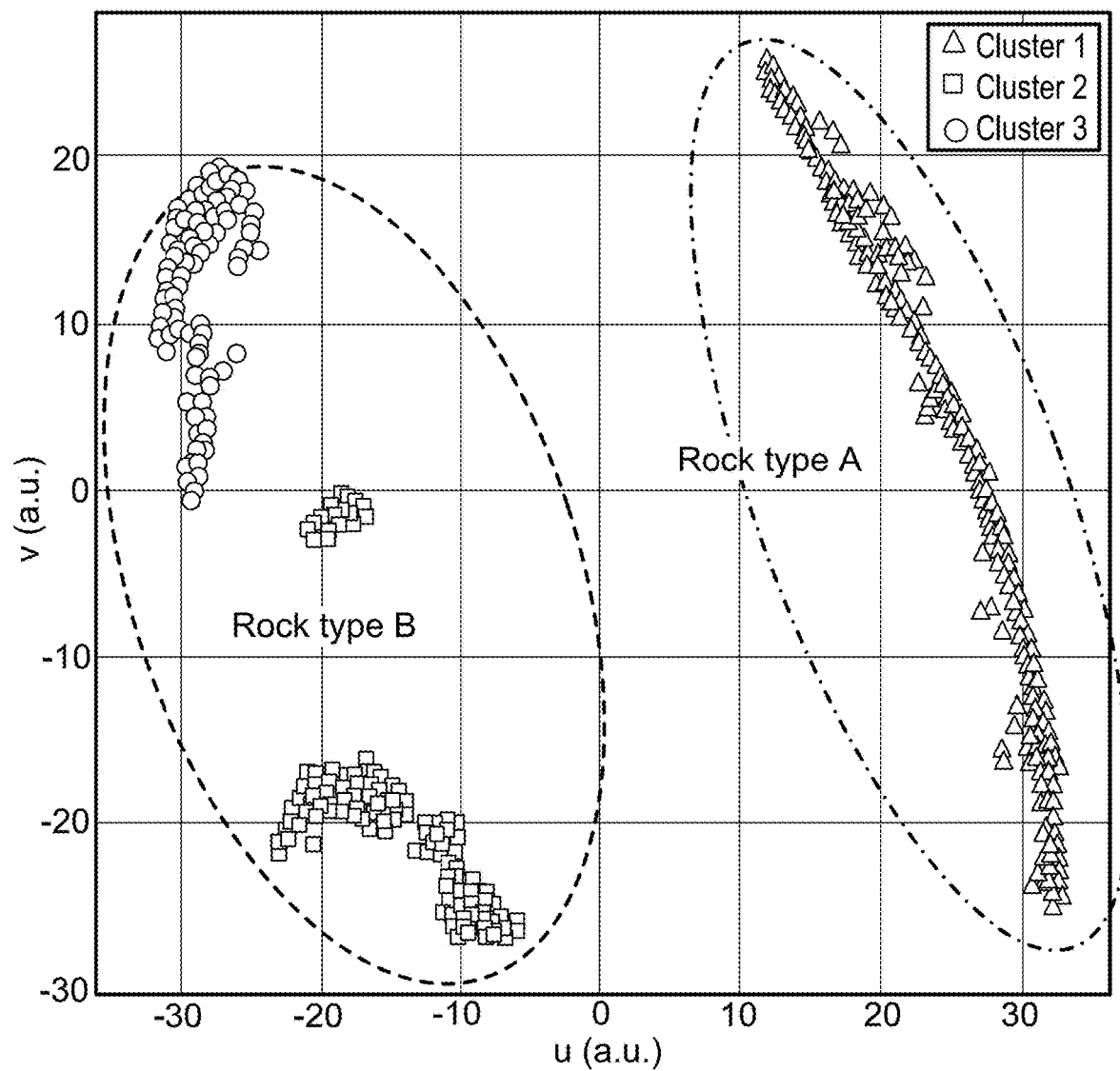
FIG. 4A illustrates examples of tSNE output for the real-time spectral data with identified clusters according to an implementation of the present disclosure.
Figure 4B:
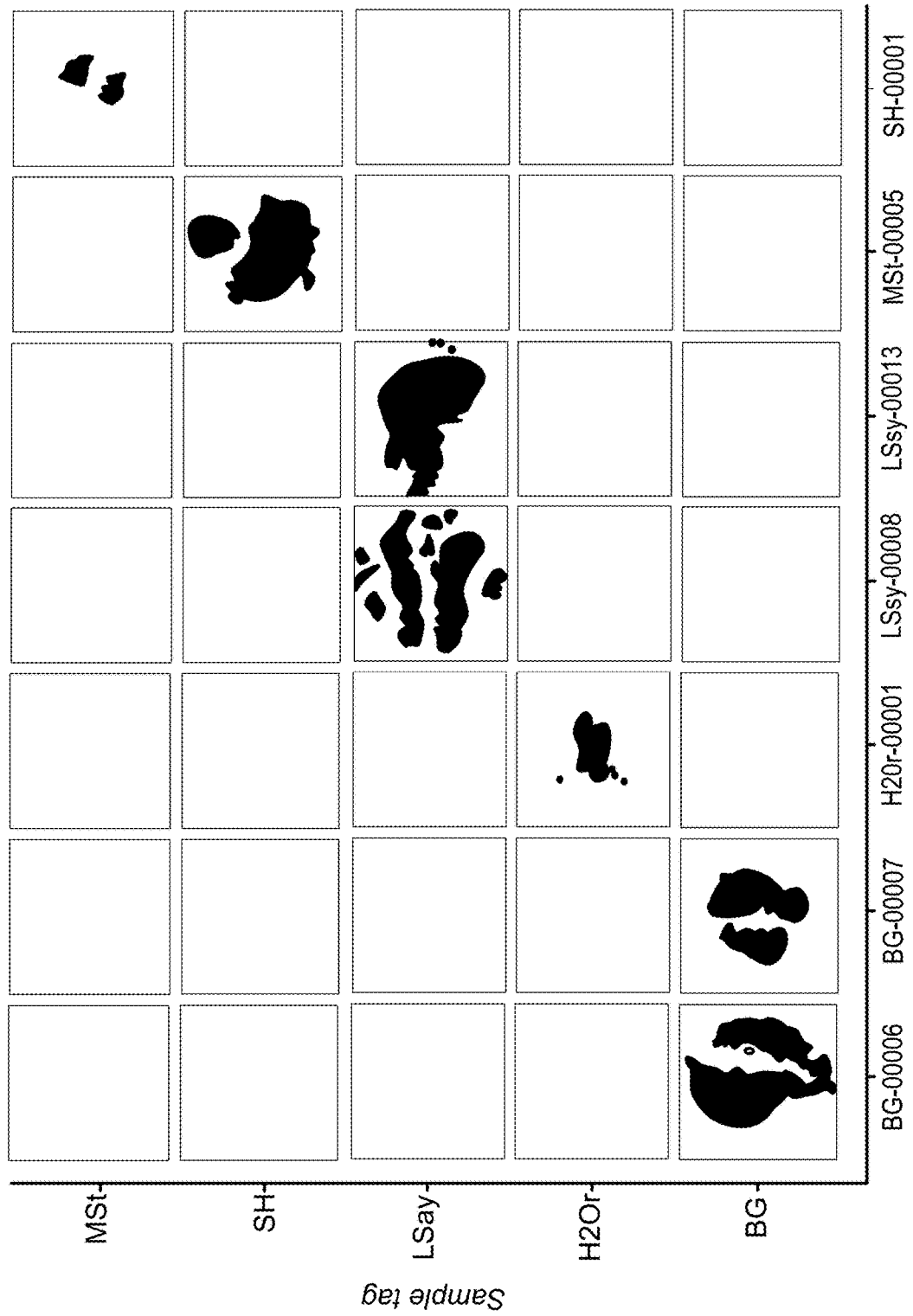
FIG. 4B illustrates examples of tSNE map of the in-line spectral data gathered during high power laser irradiation.

In more detail, the measurement data can be readily analyzed to identify rock types and assess process performance, and predict geomechanical and/or geochemical properties of the probed rock samples. For example, FIGS. 4A and 4B show the outcome of a machine learning algorithm which can use the input data (e.g., spectrum data measured as a function of wavelength) to determine the rock type. Specifically, FIG. 4A shows a clustering visualization of the real-time spectra data of a collection of samples using a technique called t-distribution stochastic neighbor embedding (t-SNE). In this example, the horizontal and vertical axes each represent a distinct arbitrary unit. The samples are grouped into 3 clusters in a two-dimensional projected space from which the rock type A (1 cluster) and rock type B (2 clusters) are fully separated, indicating successful differentiation of the two types. This analysis can be applied on new samples whose rock type can be determined based on its metric distance to each cluster centroid.

FIG. 4B shows a pairwise scatter plot between several class of sample rock types and a number of rock samples from a large number of spectra samples that have been measured and provided as input to the analysis. The horizontal axis shows the sample tags for samples from the groups of BG, H2Or, LSay, MSt, and SH. The vertical axis shows the same sample groups BG, H2Or, LSay, MSt, and SH. The results show a clear and consistent mapping between the spectra data from the physical rock samples and their rock types. Specifically, samples from the same group exhibit highly similar patterns while the patterns for samples from different groups are distinctly different.

Some implementations incorporate advanced machine learning models to map the spectra and luminosity measurements to various rock properties in addition to rock types, distributed along the measurement depth range. These models can include multichannel convolutional neural networks (MCNN) and recurrent neural networks such as long-short-time-memory (LSTM) network, which can capture both the spectral data as input features at each depth sampling point, as well as incorporating the correlation across measurement depth as determined by the formation, to produce accurate prediction of rock and subsurface properties such as geomechanical, geochemical properties and saturation, that are consistent with the subsurface formations.

The data can feed into an edge computer to identify peaks and edges and so provide a real-time monitoring of the process. Furthermore, the system could be coupled with other measurements to improve recognition performance.

Figure 5:
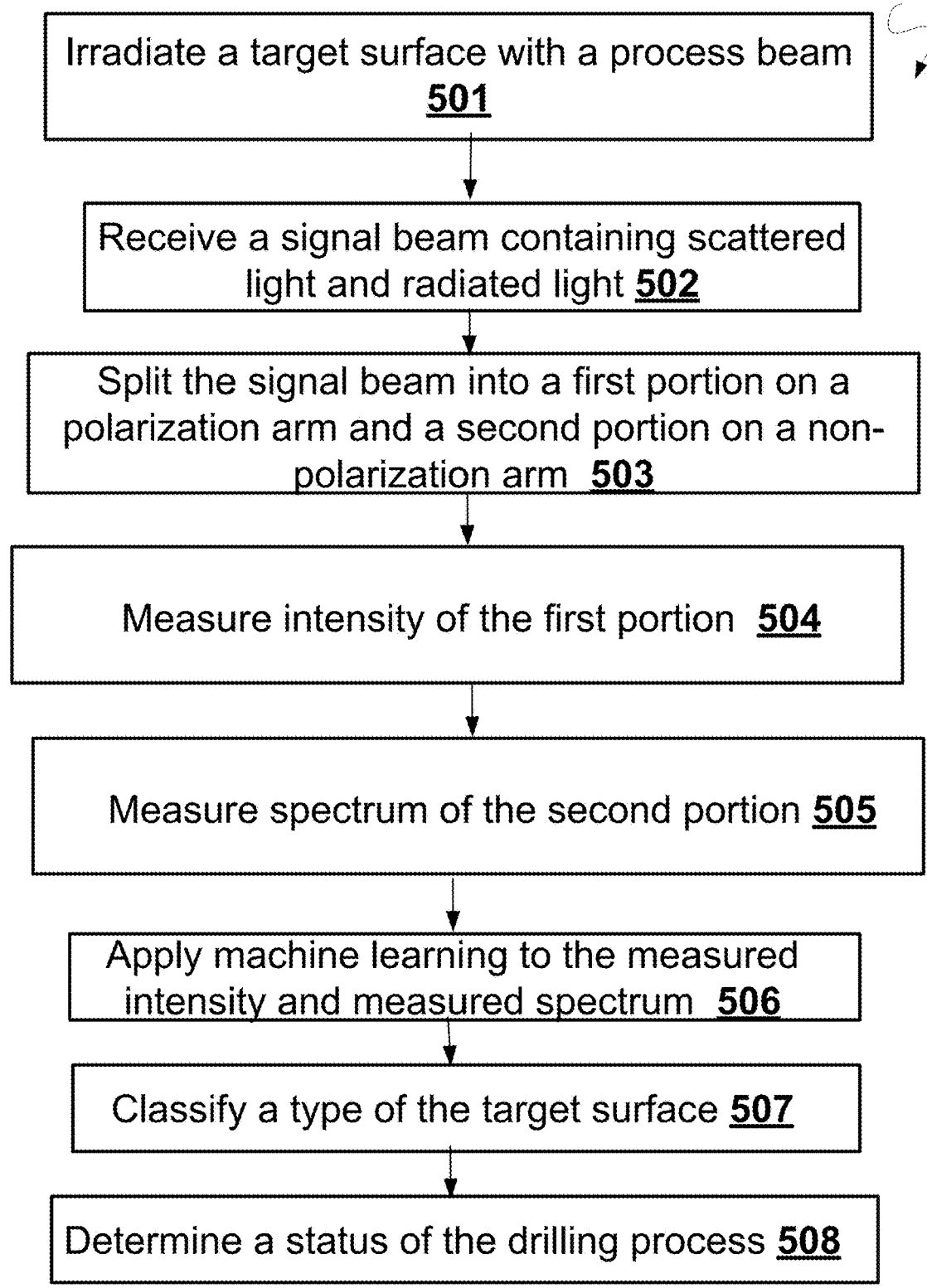
FIG. 5 illustrates an example of a flow chart according to an implementation of the present disclosure.

Some implementations can include a system with multiple modular components, such as an optical system and an analyzer. The optical system can encompass optical components such as a laser source, a polarization arm, and a non-polarization arm. The analyzer is configured to receive measurements data (such as intensity measurements and spectrum measurements) from the optical system. The analyzer can include data pre-processing module and statistical modeling module. The overall system can implement a flow chart 500 illustrated in FIG. 5 that combines photonic sensing and machine learning to assess the rock characterization and performance of the high power laser source. The flow chart may start with irradiating a target surface with a process beam (501). The process beam can be a high power laser beam provided by a pulsed or continuous wave (CW) laser source. The laser source may operate in the infrared region with a wavelength of, for example, between 600 nm and 10000 nm. Some implementations may use a laser source with a wavelength of, for example, 1064 nm. In some implementations, the process beam may encompass several laser beams at different frequencies, each capable of exciting different molecular bonds in target material.

In some cases, the high power laser beam is directed to the target surface through, for example, a prism. In these cases, the beam reflected from a surface of the prism impinges on the rock and/or downhole media, which form the target of the drilling process. The incident beam can generate a plasma and warm up the rock, both generate blackbody radiation. Additionally, light can be scattered diffusively from the target surface. The radiating light and the scattering light can be received (502) as the signal beam by, for example, the lens-coupler assembly 214 in FIG. 2B. Furthermore, the process or probe beam may be actively polarized.

Next, the signal beam is split into a first portion on a polarization arm and a second portion on a non-polarization arm (503). As illustrated in FIG. 2C, beam splitter 224 can accomplish the splitting of collimated beam 223. On the polarization arm, polarization-dependent intensity measurements can be performed on the first portion of the signal beam (504). FIG. 2C illustrates that a polarized beam splitter 226 splits the transmitted beam into cross-polarized components. In some cases, one branch of the polarization arm contains circularly left polarized light and the other branch contains circularly right polarized light. The split parts of the beam are then directed to the radiometer sensors 233A and 233B. The radiometer sensors 233A and 233B can record the intensity of each split part.

On the non-polarization arm, spectrum measurements can be performed on the second portion of the signal beam (505). As illustrated in FIG. 2C, spectrometer 229 is located at the focal plane of lens 228 so that the spectrum of the second portion of the signal beam can be measured. FIG. 2C additionally shows a beam splitter 227 that directs part of the second portion of the signal beam to CCD/CMOS sensor 231.

Figure 2D:
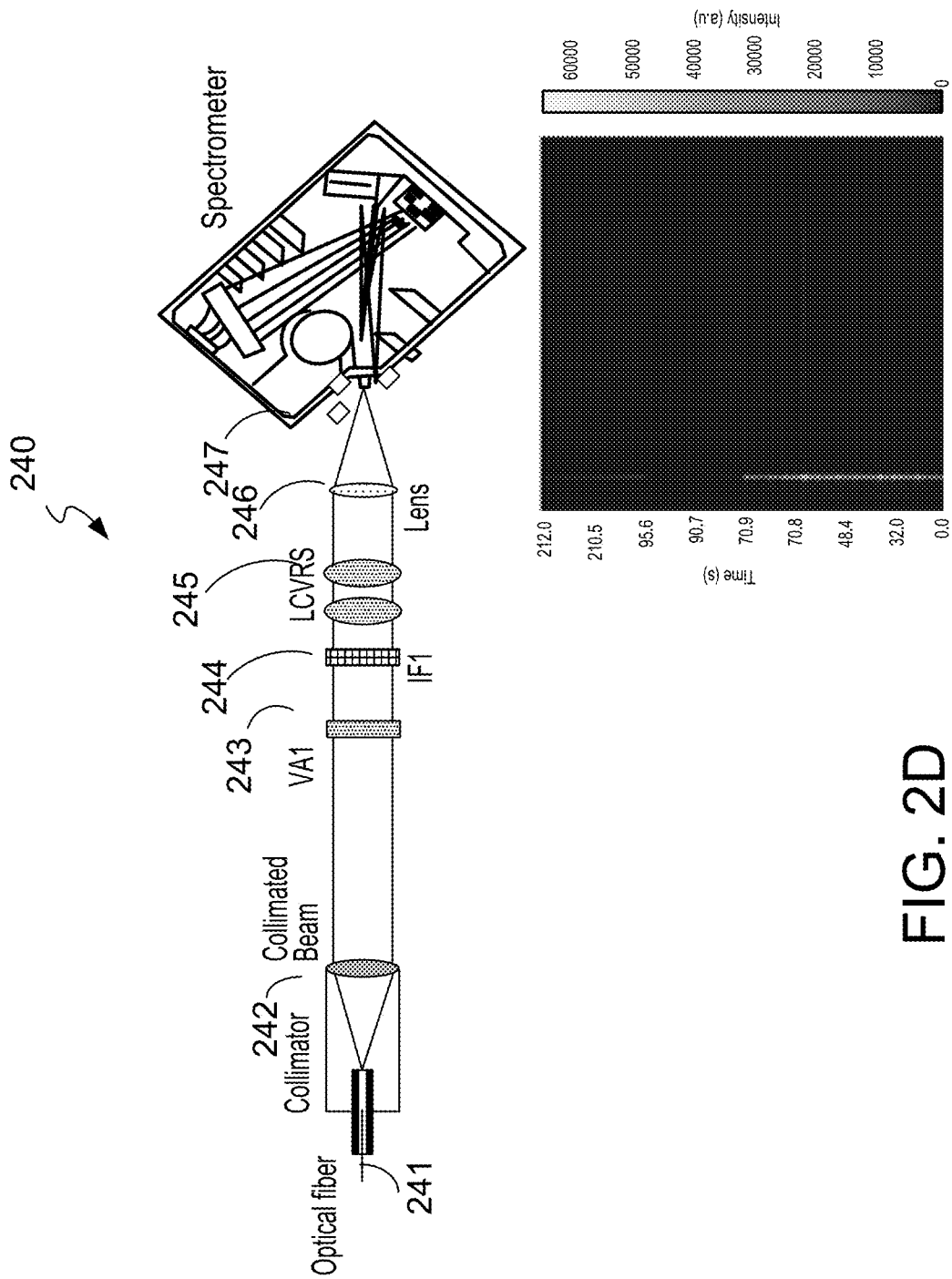
FIG. 2D is a diagram illustrating another example of a high power laser system for evaluation of overall luminosity that includes back-reflection and infrared blackbody radiation according to an implementation of the present disclosure.

Referring to FIG. 2D, some implementations may incorporate a detection system 240 for detecting signals (including back-scattered and blackbody radiation) and subsequent processing of the detected light signals. As illustrated, the signal beam is out-coupled via fiber 241 and then collimated by collimator 242 into a collimated beam. The collimated beam is then incident on variable attenuator (VA) 243 which reduces the luminosity of the beam to avoid saturation of the liquid crystal variable retarders (LCVRs) 245, and spectrometer 247. In this illustration, an active component, such as interference filter IF 244, can provide an active band pass and enable selection of the back-scattered laser beam and near-infrared radiation. LCVRs 245 can enable the selection of a given polarized mode for the incoming light beam. LCVRs 245 also can re-polarize the light in some implementations. As illustrated, lens 246 can focus the beam and couples into spectrometer 247. The spectrometer may be a scanning or Fourier-transform spectrometer. The spectrometer can characterize the beam to analyze the distribution of intensity as a function of wavelength. The LCVRs 245 can be replaced with a polarized beam splitter, which would output two beams with orthogonal polarization states. The polarized beams could each be fed to a single or dual spectrometer system. If a single spectrometer is used, then the system would need to use a chopper or other means to select which input is fed to the spectrometer. Alternatively, two spectrometers could be used to measure the spectral content of both polarization states. In either case the spectrometers could be scanning or Fourier-transform based. The analysis can be stored as well as a function of time. The time resolution may depend on the refresh-rate of the electronics and sensors in the spectrometer. Examples of the refresh rate can be around 1 ms.

Figure 2E:
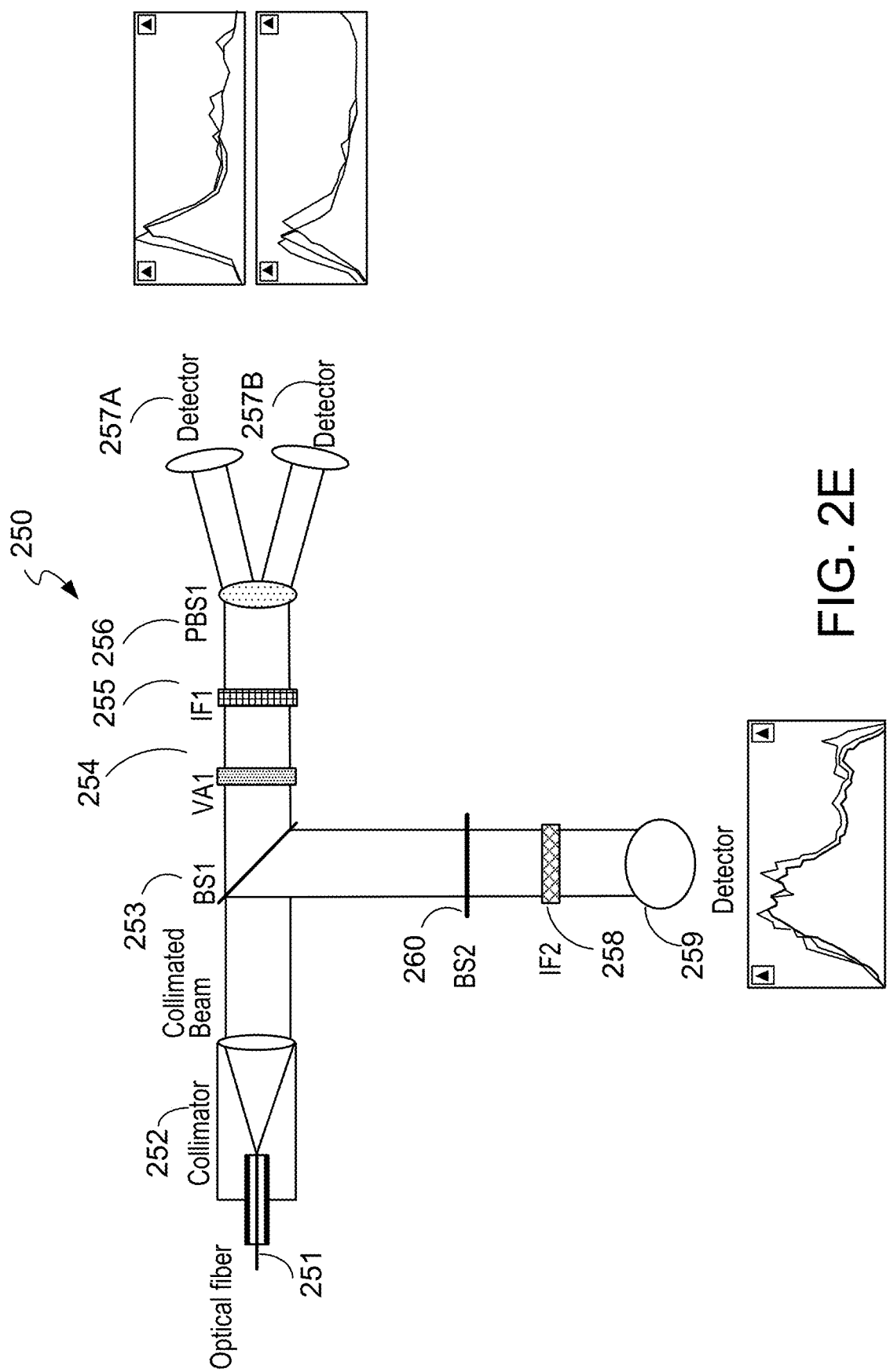
FIG. 2E is a diagram illustrating yet another example of a high power laser system for evaluation of overall luminosity that includes back-reflection and infrared blackbody radiation according to an implementation of the present disclosure.

Referring to FIG. 2E, some implementations may incorporate a detection system 250 that includes polarization-sensitive detection of light signals and subsequent processing of the detected light signals. As illustrated, the signal beam is out-coupled via fiber 251 and then collimated by collimator 252 into a collimated beam. A first beam splitter 253 splits the collimated beam into two paths for separate and parallel processing. The first path goes through a variable attenuator (VA) 254, an interference filter (IF) 255, and a polarizing-beam splitter (PBS) 256. VA 254 reduces the luminosity of the beam component and prevents saturation of the sensors downstream. IF 255 is an active component that provides a band-pass filter on the beam. This band pass filtering allows a wavelength range to pass into the next stage. IF 255 can cycle over different wavelength ranges or be fully turned-off. PBS 256 can split the transmitted beam into, for example, circular left and right polarization and directs the circularly polarized components to respective detectors 257A and 257B. Detectors 257A and 257B respectively measures the intensity distribution of the light intensity in each polarized component as a function of time.

The second path from first beam splitter 253 can address non-polarized radiance characterization. On this second path, light can through a second beam splitter (BS) 260, an active interference filter IF 258, and a detector 259. The detector 259 can measure luminosity (intensity) over time.

In FIGS. 2C-2E, the combined measurement data can be stored, processed, and analyzed in realtime or ad-posteriori. The data generated by the radiance detectors provides information about the intensity distribution of the back-scattered light. This data can be analyzed in real-time to identify rock types, material changes (e.g. change from rock to steel), identify formation of glass (left-skewed distribution), poor coupling of laser beam (left-skewed distribution in polarization dependent chart), and assess the process' performance (e.g. good performance is when most light is absorbed and no glass forms, i.e. right-skewed or centered luminosity distribution). Thus, the data can feed into an edge computer to identify peaks and edges and so provide a fast-alarm about the process. Furthermore, the system could be coupled with other measurements to improve recognition performance.

In more detail, the examples illustrated in FIGS. 2D and 2E can combine liquid crystal and interference filters for a fast analysis of spectral content per polarization channel. For example, LCVRs 245 can include a combination of liquid crystal and interference filters. LVVRs 245 can be replaced for a polarization beam splitter (PBS), which would output two orthogonally polarized beams feeding either to a single or a dual spectrometry assembly. In the case of a single spectrometer, a chopper or electronic switch could control which polarized arm is selectively analyzed. For a dual spectrometry system, the configuration could be similar to FIG. 2E, except that detectors 257A and 257B are replaced by spectrometers. In the context of high power laser transmission over long-distances, as is the case for laser drilling, the source beam red-shifts due to Raman scattering. This means that the peak wavelength of the laser may shift depending on the distance, power, fiber properties, and the environment conditions. The changes can be substantial, e.g. from an original location at about 1060 nm up to about 1200 nm. To compensate for this shift, the implementations can include tunable band-pass and edge-pass (long pass) filters. The tunable band-pass approach focuses on the spectrum of the reflected laser beam. Due to power levels present in the reflected laser beam, a Lyot filter or a Fabry-Perot resonator is often used for band-pass operation. On the other hand, the tunable long pass filter can remove the Raman-shifted laser light and enables dedicated analysis of light signals from blackbody radiation. The black-body analyzer can thus use a combination of cut-on filter at 1070 nm, plus liquid crystals or angle-tuned thin-film filters to remove the Raman-shifted laser beam.

In some cases, the black body analyzer is combined with an optical filter that can discriminate between coherent/incoherent light. Given that the coherence length of the laser light is significantly longer than the light emitted from blackbody radiation, the optical filter can include a single filtering element to discriminate between both. In various implementations, the optical filter can be designed to include reflecting surfaces tilted with respect to one another slightly by an angle $\theta$. This condition imposes a separation between filters: $S > D/(\tan 2\theta + \tan 4\theta)$, where D is the diameter of the filter. For context, the backscatter light and the blackbody radiation may overlap in frequency, which means that the band-pass filter alone may not be able to remove the laser light. The optical filter can be introduced to remove the laser backscattered light from the blackbody radiation. The optical filter can use two tilted long-pass filters separated a distance S. Such considerations of differentiating coherence/incoherence light can also apply to the luminosity sensor.

Some implementations may further include a feedback loop between the spectrometer and a tunable filter. By way of illustration, the Raman shift depends on multiple parameters, which can be difficult to account for a priori. In the example of FIG. 2D, the spectrometer 247 can identify the wavelengths of peak power. Thereafter, detection system 240 may use a coherent filter and a band-pass filter to scan the spectrum, and then select the appropriate cut on frequency for the tunable filter. The frequency red-shift of the laser may also drift over time. For this reason, the feedback loop may continue to operate during the monitoring process so that adjustment can be applied to the tunable filter.

Subsequently, machine learning techniques can be applied to the measured intensity and the measured spectrum (506). For example, a controller device in communication with the laser source, the polarization arm, and the non-polarization arm can apply machine learning techniques to identify a first set of features from the polarization-dependent intensity measurements from the polarization arm and a second set of features from the spectrum measurements from the non-polarization arm. The features can then be combined and weighted when determining a classification of the target surface (507) or a status of the drilling process (508). For example, the first set and the second set can be selected features that more significantly correlate with a particular material classification or a particular process status. Indeed, a database of the selected sets of features can be established and maintained with more and more measurement data. Some implementations can apply the database to select features when processing newly obtained measurement data. Examples of machine learning techniques include: a boosting technique, a K-means clustering technique, and a Support Vector Machine (SVM) technique. In some cases, the classification of the target surface can be visualized using a t-distribution stochastic neighbor embedding (tSNE) technique. The controller device can include a computer system. The computer system can incorporate, for example, analyzer 216 of FIG. 2B.

Figure 6:
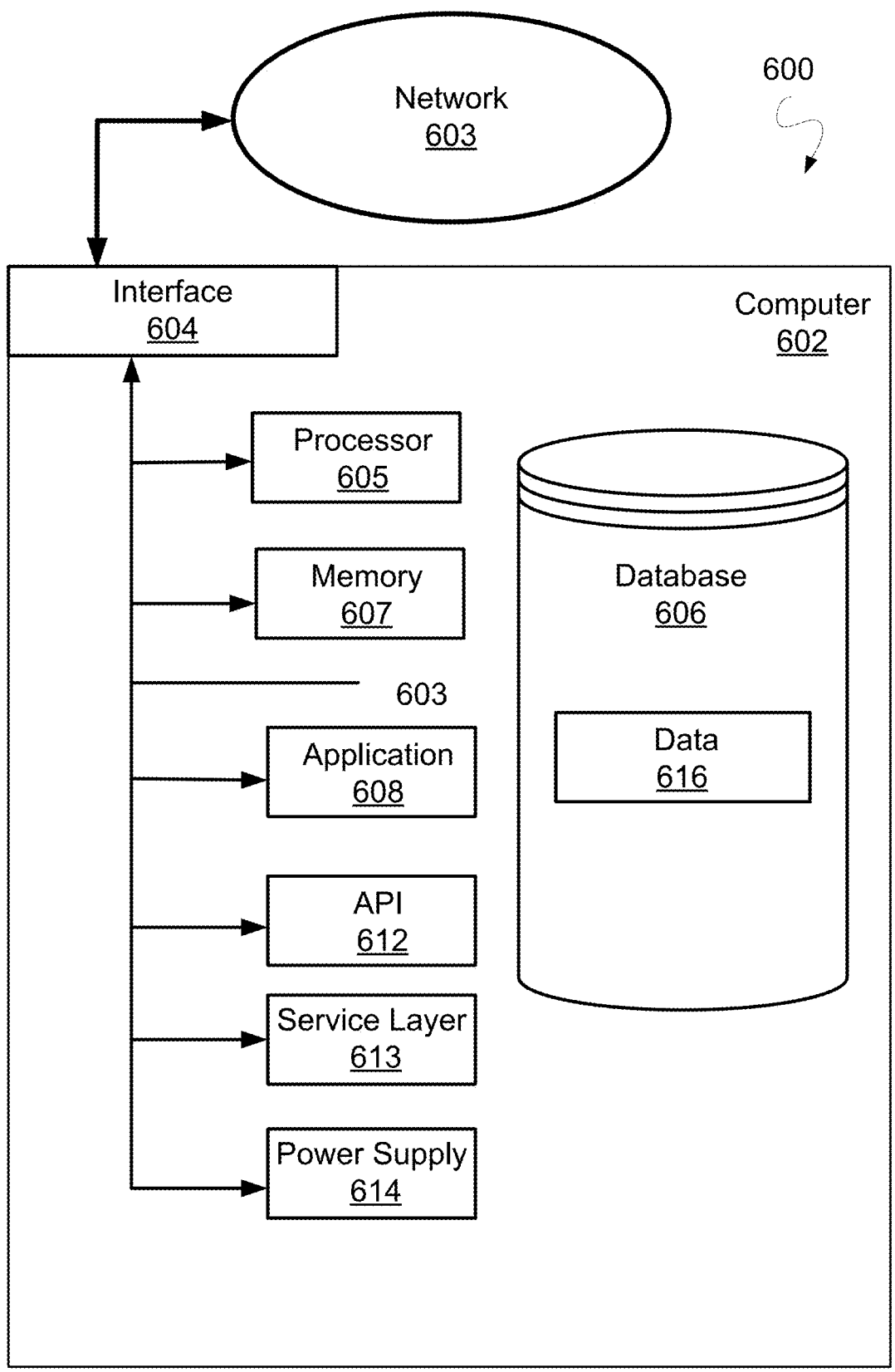
FIG. 6 is a block diagram illustrating an example of a computer system used to provide computational functionalities associated with described algorithms, methods, functions, processes, flows, and procedures, according to an implementation of the present disclosure.

FIG. 6 is a block diagram illustrating an example of a computer system 600 used to provide computational functionalities associated with described algorithms, methods, functions, processes, flows, and procedures, according to an implementation of the present disclosure. The illustrated computer 602 is intended to encompass any computing device such as a server, desktop computer, laptop/notebook computer, wireless data port, smart phone, personal data assistant (PDA), tablet computing device, one or more processors within these devices, another computing device, or a combination of computing devices, including physical or virtual instances of the computing device, or a combination of physical or virtual instances of the computing device. Additionally, the computer 602 can comprise a computer that includes an input device, such as a keypad, keyboard, touch screen, another input device, or a combination of input devices that can accept user information, and an output device that conveys information associated with the operation of the computer 602, including digital data, visual, audio, another type of information, or a combination of types of information, on a graphical-type user interface (UI) (or GUI) or other UI.

The computer 602 can serve in a role in a computer system as a client, network component, a server, a database or another persistency, another role, or a combination of roles for performing the subject matter described in the present disclosure. The illustrated computer 602 is communicably coupled with a network 603. In some implementations, one or more components of the computer 602 can be configured to operate within an environment, including cloud-computing-based, local, global, another environment, or a combination of environments.

The computer 602 is an electronic computing device operable to receive, transmit, process, store, or manage data and information associated with the described subject matter. According to some implementations, the computer 602 can also include or be communicably coupled with a server, including an application server, e-mail server, web server, caching server, streaming data server, another server, or a combination of servers.

The computer 602 can receive requests over network 603 (for example, from a client software application executing on another computer 602) and respond to the received requests by processing the received requests using a software application or a combination of software applications. In addition, requests can also be sent to the computer 602 from internal users, external or third-parties, or other entities, individuals, systems, or computers.

Each of the components of the computer 602 can communicate using a system bus 603. In some implementations, any or all of the components of the computer 602, including hardware, software, or a combination of hardware and software, can interface over the system bus 603 using an application programming interface (API) 612, a service layer 613, or a combination of the API 612 and service layer 613. The API 612 can include specifications for routines, data structures, and object classes. The API 612 can be either computer-language independent or dependent and refer to a complete interface, a single function, or even a set of APIs. The service layer 613 provides software services to the computer 602 or other components (whether illustrated or not) that are communicably coupled to the computer 602. The functionality of the computer 602 can be accessible for all service consumers using this service layer. Software services, such as those provided by the service layer 613, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the computer 602, alternative implementations can illustrate the API 612 or the service layer 613 as stand-alone components in relation to other components of the computer 602 or other components (whether illustrated or not) that are communicably coupled to the computer 602. Moreover, any or all parts of the API 612 or the service layer 613 can be implemented as a child or a sub-module of another software module, enterprise application, or hardware module without departing from the scope of the present disclosure.

The computer 602 includes an interface 604. Although illustrated as a single interface 604 in FIG. 6, two or more interfaces 604 can be used according to particular needs, desires, or particular implementations of the computer 602. The interface 604 is used by the computer 602 for communicating with another computing system (whether illustrated or not) that is communicatively linked to the network 603 in a distributed environment. Generally, the interface 604 is operable to communicate with the network 603 and comprises logic encoded in software, hardware, or a combination of software and hardware. More specifically, the interface 604 can comprise software supporting one or more communication protocols associated with communications such that the network 603 or interface's hardware is operable to communicate physical signals within and outside of the illustrated computer 602.

The computer 602 includes a processor 605. Although illustrated as a single processor 605 in FIG. 6, two or more processors can be used according to particular needs, desires, or particular implementations of the computer 602. Generally, the processor 605 executes instructions and manipulates data to perform the operations of the computer 602 and any algorithms, methods, functions, processes, flows, and procedures as described in the present disclosure.

The computer 602 also includes a database 606 that can hold data for the computer 602, another component communicatively linked to the network 603 (whether illustrated or not), or a combination of the computer 602 and another component. For example, database 606 can be an in-memory, conventional, or another type of database storing data consistent with the present disclosure. In some implementations, database 606 can be a combination of two or more different database types (for example, a hybrid in-memory and conventional database) according to particular needs, desires, or particular implementations of the computer 602 and the described functionality. Although illustrated as a single database 606 in FIG. 6, two or more databases of similar or differing types can be used according to particular needs, desires, or particular implementations of the computer 602 and the described functionality. While database 606 is illustrated as an integral component of the computer 602, in alternative implementations, database 606 can be external to the computer 602. As illustrated, the database 606 holds the previously described data 616 including, for example, multiple streams of data from various sources, such as the intensity measurements, spectrum measurements, and CCD/CMOS readout as outlined in FIG. 2C.

The computer 602 also includes a memory 607 that can hold data for the computer 602, another component or components communicatively linked to the network 603 (whether illustrated or not), or a combination of the computer 602 and another component. Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 or similar or differing types can be used according to particular needs, desires, or particular implementations of the computer 602 and the described functionality. While memory 607 is illustrated as an integral component of the computer 602, in alternative implementations, memory 607 can be external to the computer 602.

The application 608 is an algorithmic software engine providing functionality according to particular needs, desires, or particular implementations of the computer 602, particularly with respect to functionality described in the present disclosure. For example, application 608 can serve as one or more components, modules, or applications. Further, although illustrated as a single application 608, the application 608 can be implemented as multiple applications 608 on the computer 602. In addition, although illustrated as integral to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion or management circuits (including recharging, standby, or another power management functionality). In some implementations, the power-supply 614 can include a power plug to allow the computer 602 to be plugged into a wall socket or another power source to, for example, power the computer 602 or recharge a rechargeable battery.

There can be any number of computers 602 associated with, or external to, a computer system containing computer 602, each computer 602 communicating over network 603. Further, the term "client," "user," or other appropriate terminology can be used interchangeably, as appropriate, without departing from the scope of the present disclosure. Moreover, the present disclosure contemplates that many users can use one computer 602, or that one user can use multiple computers 602.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to a receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and apparatus can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of media and memory devices, magnetic devices, magneto optical disks, and optical memory device. Memory devices include semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Magnetic devices include, for example, tape, cartridges, cassettes, internal/removable disks. Optical memory devices include, for example, digital video disc (DVD), CD-ROM, DVD+/−R, DVD-RAM, DVD-ROM, HD-DVD, and BLURAY, and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback. Input from the user can be received in any form, including acoustic, speech, or tactile input. In addition, a computer can interact with the user by sending documents to and receiving documents from a client computing device that is used by the user.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, Frame Relay frames, Asynchronous Transfer Mode (ATM) cells, voice, video, data, or other information between networks addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what can be claimed, but rather as descriptions of features that can be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A method comprising:
   irradiating a target surface with a process beam from a laser source during a drilling process;
   in response to irradiating with the process beam, receiving, using a lens-coupler assembly, a signal beam that contains light scattered from the target surface as well as light radiating from the target surface;
   splitting, using a beam splitter, the signal beam into a first portion on a first arm and a second portion on a second arm, wherein the first portion is further split, by a polarized beam splitter on the first arm, into a first sub-portion of circularly left polarized light and a second sub-portion of circularly right polarized light, and wherein the second portion of the signal beam is unpolarized on the second arm;
   performing, on the first arm, a first plurality of intensity and spectrum measurements of the first sub-portion of circularly left polarized light and the second sub-portion of circularly right polarized light, using a device selected from a radiometer sensor and a spectrometer;
   performing, on the second arm, a second plurality of intensity and spectrum measurements of the second portion using a device selected from a spectrometer, a charge-coupled device, and a complementary metal-oxide-semiconductor sensor, or any combination thereof; and
   determining, using a controller device that is in communication with the laser source, the first arm, and the second arm, a classification of the target surface based on applying, by the controller device, one or more machine learning techniques to at least portions of (i) the first plurality of intensity and spectrum measurements, and (ii) the second plurality of intensity and spectrum measurements.

2. The method of claim 1, further comprising:
   determining a status of the drilling process; and
   predicting at least one of: a type of an incoming rock, an outcome of the drilling process, a parameter for performing the first plurality of polarization-dependent intensity and spectrum measurements, or a parameter for performing the second plurality of intensity and spectrum measurements.

3. The method of claim 1, wherein the one or more machine learning techniques comprise:
   identifying a first set of features from the first plurality of intensity and spectrum measurements and a second set of features from the second plurality of intensity and spectrum measurements; and
   combining the first set of features and the second set of features in determining the classification of the target surface.

4. The method of claim 3, further comprising:
   establishing a database of the first set of features and the second set of features, wherein the first set of features and the second set of features in combination differentiate two or more types of the target surface.

5. The method of claim 4, further comprising:
   applying the database while applying the one or more machine learning techniques to the at least portions of (i) the first plurality of intensity and spectrum measurements, and (ii) the second plurality of intensity and the spectrum measurements.

6. The method of claim 1, wherein the one or more machine learning techniques include: a boosting technique, a K-means clustering technique, and a Support Vector Machine (SVM) technique.

7. The method of claim 1, further comprising:
visualizing the classification of the target surface using a t-distribution stochastic neighbor embedding (tSNE) technique.

8. The method of claim 1, wherein the first plurality of polarization-dependent intensity and spectrum measurements comprise first intensity measurements on a first branch and second intensity measurements on a second branch,
wherein the first and second intensity measurements are cross-polarized, and
wherein the first and second branches originate from a polarization beam splitter on the polarization arm.

9. The method of claim 1, further comprising:
capturing, on the non-polarization arm, a plurality of images based on the second portion of the signal beam; and
determining a luminosity based on a histogram of the plurality of images.

10. The method of claim 9, further comprising:
applying the one or more machine learning techniques to the luminosity in addition to the at least portions of (i) the first plurality of polarization-dependent intensity and spectrum measurements, and (ii) the second plurality of intensity and spectrum measurements; and
based on results from the one or more machine learning techniques, determining at least one of: a classification of the target surface and a status of the drilling process.

11. A high-power laser system comprising:
an optical system that includes:
a laser source that emits a process beam;
a first arm that receives a portion of a signal beam, the first arm comprising a polarizing beam splitter; and
a second arm that receives another portion of the signal beam; and
an analyzer in communication with optical system, wherein the analyzer receives measurement data from the optical system,
wherein the high-power laser system is configured to perform operations of:
irradiating a target surface with a process beam from the laser source during a drilling process;
in response to irradiating with the process beam, receiving, using a lens-coupler assembly, a signal beam that contains light scattered from the target surface as well as light radiating from the target surface;
splitting, using a beam splitter, the signal beam into a first portion on a first arm and a second portion on a second arm, wherein the first portion is further split, by the polarized beam splitter on the first arm, into a first sub-portion of circularly left polarized light and a second sub-portion of circularly right polarized light, and wherein the second portion of the signal beam is unpolarized on the second arm;
performing, on the first arm, a first plurality of intensity and spectrum measurements of the first sub-portion of circularly left polarized light and the second sub-portion of circularly right polarized light, using a device selected from a radiometer sensor and a spectrometer;
performing, on the second arm, a second plurality of intensity and spectrum measurements of the second portion using a device selected from a spectrometer, a charge-coupled device, and a complementary metal-oxide-semiconductor sensor, or any combination thereof; and
determining, using a controller device that is in communication with the laser source, the first arm, and the second arm, a classification of the target surface based on applying, by the controller device, one or more machine learning techniques to at least portions of (i) the first plurality of intensity and spectrum measurements, and (ii) the second plurality of intensity and spectrum measurements.

12. The system of claim 11, wherein the operations further comprise:
determining a status of the drilling process; and
predicting at least one of: a type of an incoming rock, an outcome of the drilling process, a parameter for performing the first plurality of polarization-dependent intensity and spectrum measurements, or a parameter for performing the second plurality of intensity and spectrum measurements.

13. The high-power laser system of claim 11, wherein the one or more machine learning techniques comprise:
identifying a first set of features from the first plurality of intensity and spectrum measurements and a second set of features from the second plurality of intensity and spectrum measurements; and
combining the first set of features and the second set of features in determining the classification of the target surface.

14. The high-power laser system of claim 13, wherein the operations further comprise:
establishing a database of the first set of features and the second set of features, wherein the first set of features and the second set of features in combination differentiate two or more types of the target surface.

15. The high-power laser system of claim 14, wherein the operations further comprise:
applying the database while applying the one or more machine learning techniques to the at least portions of (i) the first plurality of intensity and spectrum measurements, and (ii) the second plurality of intensity and spectrum measurements.

16. The high-power laser system of claim 11, wherein the one or more machine learning techniques include: a boosting technique, a K-means clustering technique, and a Support Vector Machine (SVM) technique.

17. The system of claim 11, wherein the operations further comprise:
visualizing the classification of the target surface using a t-distribution stochastic neighbor embedding (tSNE) technique.

18. The system of claim 11, wherein the first plurality of polarization-dependent intensity and spectrum measurements comprise first intensity measurements on a first branch and second intensity measurements on a second branch,
wherein the first and second intensity measurements are cross-polarized, and
wherein the first and second branches originate from a polarization beam splitter on the polarization arm.

19. The system of claim 11, wherein the operations further comprise:
    capturing, on the non-polarization arm, a plurality of images based on the second portion of the signal beam; and
    determining a luminosity based on a histogram of the plurality of images.

20. The system of claim 19, wherein the operations further comprise:
    applying the one or more machine learning techniques to the luminosity in addition to the first plurality of polarization-dependent intensity and spectrum measurements, and the second plurality of intensity and spectrum measurements; and
    based on results from the one or more machine learning techniques, determining at least one of: a classification of the target surface and a status of the drilling process.

* * * * *